United States Patent [19]

Villari et al.

[11] Patent Number: 4,913,161

[45] Date of Patent: Apr. 3, 1990

[54] BAG-TILT INDICATOR ON URINE BAG

[75] Inventors: Frank Villari, Oak Park; Brian H. Silver, Hoffman Estates, both of Ill.

[73] Assignee: The Kendall Company, Boston, Mass.

[21] Appl. No.: 137,275

[22] Filed: Dec. 23, 1987

[51] Int. Cl.⁴ .............................................. A61M 1/00
[52] U.S. Cl. .................................... 128/766; 604/323; 604/361
[58] Field of Search ........................ 604/318, 322–325, 604/360, 361, ; 128/766, 767, 771, 760, 762; 73/215; 116/206; 422/119

[56] References Cited

U.S. PATENT DOCUMENTS

| Re. 26,964 | 10/1970 | Coanda | 128/776 |
| 3,004,895 | 10/1961 | Schwartz | 604/360 |
| 3,601,119 | 8/1971 | Engelsher | 604/323 |
| 4,095,589 | 6/1978 | Manschot et al. | 128/767 |
| 4,622,981 | 11/1986 | Sherlock | 604/322 |

Primary Examiner—Jerome L. Kruter
Attorney, Agent, or Firm—Alvin Isaacs

[57] ABSTRACT

The present invention comprises a urine collection bag with a tilt bag indicator on the front wall thereof. The indicator comprises a clear patch or housing disposed to the side of the input conduit of the containment bag. An orifice is disposed through the front wall to provide communication between the chamber of the collection bag and the chamber defined by the transparent patch and the front wall of the bag. If the bag is tilted, urine will escape the collection bag chamber and go into the indicator chamber, and be trapped there. This will alert appropriate medical personnel that a reflux of urine up the input conduit, thus allowing whatever corrective action be taken, as necessary.

12 Claims, 1 Drawing Sheet

BAG-TILT INDICATOR ON URINE BAG

BACKGROUND OF THE INVENTION

1. Field of the Invention

This invention relates to urine collection bags and more particularly to a tilt indicator arranged onto the walls of a urine collection bag.

2. Prior Art

Urine collection from a patient usually involves catheterization wherein a catheter is placed in the patient such that is communicates with the patient's bladder, and during catheterization urine drains from the bladder through the catheter and a drainage tube to the collection bag for retention therein. Such systems should be closed to the atmosphere to minimize the possibility of contamination. Nonetheless, a persistent problem remains, in that the collected urine in the bag may become contaminated, which could result in undesirable retrograde bacteria movement through the system to the bladder of the patient.

Urine bags for this reason, should always be kept below the patient's bladder. Some collection bags have anti-reflux valves in their flowpaths to prevent or minimize the likelihood of reflux of urine from the bag to the bladder if the bag is tipped or if the bag is inadvertently placed above the bladder.

An anti-reflux valve of this type is shown in U.S. Pat. No. 4,490,144 to Steigerwald, wherein a disc member is movably closable against an aperture, when its containment bag is improperly moved.

It is desirable however, to have a collection bag which will indicate if it actually has been improperly tipped, any anti-reflux system notwithstanding.

Thus, it is an object of the present invention to provide a reflux indicator in the fill system, to provide a signal to appropriate medical personnel that the bag has been tipped, and that appropriate action may have to be undertaken. The reflux indicator also tends to discourage mishandling of the collection bag by medical personnel who might otherwise tend to rely on an anti-reflux valve.

BRIEF SUMMARY OF THE INVENTION

The present invention comprises a collection bag for the receipt and containment of body fluids such as urine. The bag includes a hollow connector portion which extends from a drainage tube connected to a catheter attached to a patient. The hollow connector portion includes a drip chamber which is in fluid communication through an inlet port, with the collection bag.

The collection bag has a front and a rear wall, sealed at their common peripheries. The inlet port is on the front wall of the collection bag.

A tilt indicator chamber is disposed on the front wall of the collection bag. The tilt indicator chamber comprises a flexible clear patch of plastic material sealed all around its periphery, to the outside of the front wall.

An orifice is disposed through the front wall of the container bag, within the boundary defined by the indicator chamber, and near but spaced from the top edge thereof. The orifice and chamber are disposed to one side of the front wall, as so not to be beneath the inlet port of the collection bag.

A vent is arranged through the indicator chamber itself. The chamber vent is constructed of a hydrophobic material which permits air but not fluid to pass therethrough. The chamber vent permits the indicator chamber to be more sensitive by more readily allowing fluid to enter the indicator chamber without any bubble or back pressure blocking its entry.

The indicator chamber is utilized to receive urine from the contents of the bag if the collection bag is inadvertently tipped too far, or is lain on its side, so as to permit the possibility of reflux of potentially contaminated urine into the drip chamber and catheter attached to the patient.

The chamber retains the urine therein so as to alert appropriate personnel that such a reflux may have occurred.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
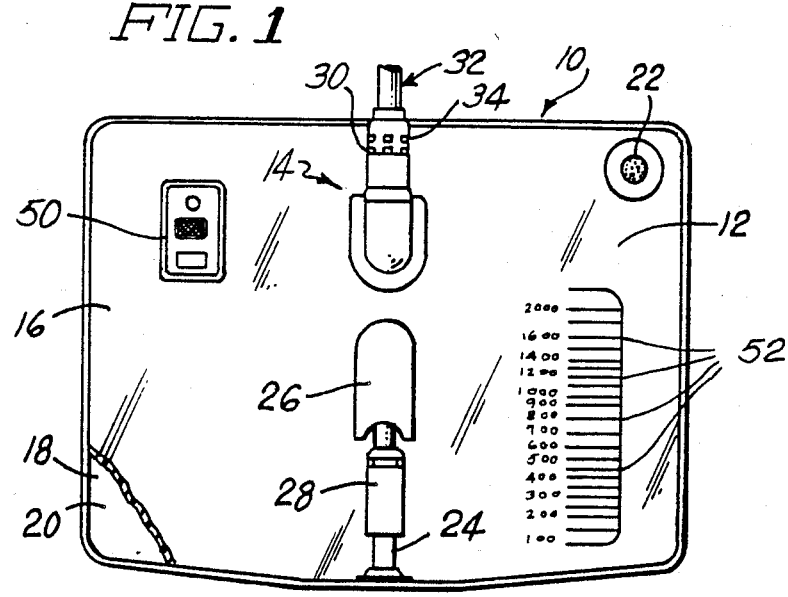
FIG. 1 is a fragmentary front plan view of a collection device of the present invention.

Referring now to the drawings in detail, and particularly to FIG. 1, there is shown a body fluid collection device 10, comprising a container 12 and a connector means 14.

The container 12 has a front wall 16 and a back wall 18 of suitable flexible plastic material joined together at their peripheral edges of the front and back walls 16 and 18 to define a chamber 20 in the container 12. The container 12 may have a vent 22 with a bacteria filter of known type to filter bacteria passing from the atmosphere into the container chamber 20.

The container 12 may have a tubular section 24 attached to a lower portion of the container front wall 16 and communicating with the chamber 20, with an outer end of the tubular section 24 being receivable in a pocket 26 on the front wall 16 in a storage position of the tubular section 24. The tubular section 24 may have a suitable clamp 28 which prevents passage of urine through the tubular section 24 when the clamp 28 is closed. When it is desired to drain urine from the container chamber 20, the outer end of the tubular section 24 is removed from the pocket 26, and the clamp 28 may be opened in order to permit passage of urine through the tubular section 24. The clamp 28 is thereafter closed and the tubular section 24 is again inserted into the pocket 26 in the storage position of the tubular section 24.

The connector means 14 is hollow, and is in the form of a drip chamber 30 attached to the front wall 16 of the container 12 and communicating with the container chamber 20. As shown, the upper portion of the drip chamber 20 is attached to the lower end of a drainage tube 32, such that the drainage tube 32 provides fluid communication therewith. If desired, the drip chamber 30 may have a vent 34 with a bacteria filter of known hydrophobic type to filter bacteria from air passing from the atmosphere into the connector means 14 through the vent 34.

The drip chamber 30 is of tubular construction and is utilized normally in a vertical orientation with respect to the patient. The drip chamber 30 mates with an inlet port 36 which itself is fixedly attached to the front wall 16 of the container 12. The inlet port 36 is an L-shaped conduit which provides the fluid communication between the drip chamber 30 and the container chamber 20. The drip chamber 30 extends downwardly into the uppermost distal end of the inlet port 36, and terminates inside the inlet port 36.

Figure 2:
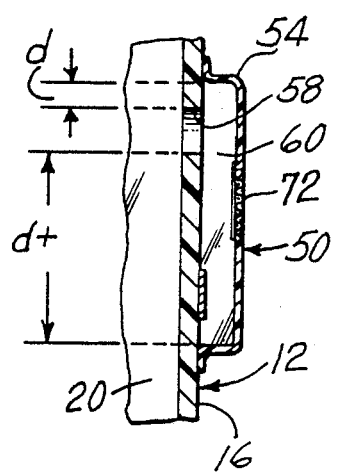
FIG. 2 is a sectional view taken along the lines II—II of FIG. 1.

The bag-tilt indicator 50 is arranged in the front wall 16 of the container bag 12, as shown in FIGS. 1 and 2. The front wall 16 has a plurality of graduated volume marks 52 thereon. The tilt indicator 50 is located above the highest normal volume content mark 52, so that urine would not spill into the indicator 50 when the container 12 is full or less than full, unless of course, the container is tilted too far or laid on its side. The tilt indicator 50 is also attached to the left or right side portion of the front wall 16 (left as shown in FIG. 1), so as to be free of the running of urine as it drains down the inside front wall 16 from the inlet port 36.

The tilt indicator 50 may be comprised of a clear plastic cup shaped housing, or a blister type patch 54, as shown in FIG. 2. The patch 54 (or the cup shaped housing, not shown) has a peripheral lip 56 which is secured by a known means such as adhesive or heat sealing, to the appropriate location on the front wall 16 of the container bag 12. An orifice 58 is disposed through the front wall 16, so as to provide fluid communication with the chamber 60 disposed between the path 54 and the wall 16. The orifice 58 is spaced a distance "d" from the top of the patch 54 but is closer to the top than from the bottom, a distance "d+", as shown in FIG. 2. This will permit any urine in the chamber 60 to stay in there, and not leak out before appropriate medical personnel have noticed that it contains any fluid, so as to enable them to take whatever remedial action is necessary.

Figure 3:
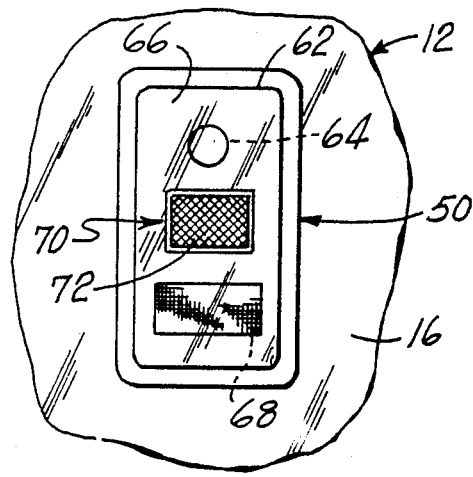
FIG. 3 is a front view of a tilt indicator, in a further embodiment thereof.

A further embodiment of the tilt indicator 50 is shown in FIG. 3, wherein a clear plastic path or clear housing 62 is shown secured to the front wall 16. An orifice 64 is arranged through the wall 16 to provide fluid communication between the chamber 20 of the fluid collection bag 12, and a chamber 66 between the wall 16 and the patch or housing 62. A urine indicator 68, such as a colored sponge or a table of food coloring, preferably having antibacterial or antimicrobial capabilities, which are known in the art, is disposed in the chamber 66 in the housing or patch 62, to more significantly identify any fluid in that chamber. A vent 70 may be arranged through the indicator 50. The chamber vent 70 is constructed of a hydrophobic material 72 which allows air to pass through, but not liquid. The chamber vent 70 may be a substitute for the vent 22 on the wall 16 of the container 12. The hydrophobic material 72 may be a fluorocarbon base flexible sheet of material marketed under the Trademark "Coretex" or "Porex" or the like. The chamber vent 70 permits the chamber 50 to be more sensitive and receptive to the influx of fluid therein.

Thus, what has been shown is an inexpensive means for indicating that a urine collection bag has been tilted too far to one side, or has been lain on one side, which might permit a reflux of urine therein, into the drainage system leading to the patient to which it is attached.

We claim:

1. A tilt bag indicating device for a urine collection bag which receives a volume of urine from a patient, comprising:
   a container having a drainage tube and a chamber for receipt of urine, said chamber being defined by a back wall and a front wall joined at their common periphery;
   a connector means for conducting fluid from the drainage tube to said chamber of the container;
   an indicator means having dimensions substantially smaller than the container and arranged on the front wall of said container to define an indicator chamber to receive and trap urine therein, if said container is tipped on its side with urine therein;
   an orifice disposed through said front wall adjacent said indicating means to permit fluid communication between the chamber of the container and said indicator chamber; and
   a vent disposed through said indicating device establishing sensitivity of said indicating device during the tilting thereof.

2. A tilt bag indicating device as recited in claim 1, wherein said indicating means comprises a transparent path secured to said front wall at the periphery of said patch.

3. A tilt bag indicating device as recited in claim 1, wherein said orifice is spaced from the top of said patch.

4. A tilt bag indicating device as recited in claim 3, wherein said orifice is spaced further from the bottom of said patch than from the top of said patch.

5. A tilt bag indicating device as recited in claim 3, wherein said indicating means is disposed to the side of said connector means arranged in the front wall of said collection bag.

6. A tilt bag indicating device as recited in claim 1, wherein said indicating means comprises a cup shaped transparent housing to define an indicating chamber between said housing and said front wall.

7. A tilt bag indicating device as recited in claim 1, wherein said indicating means is disposed above the normal volume of urine contained in said containment bag.

8. A tilt bag indicating device as recited in claim 1, wherein a fluid indicating member is disposed in said indicating chamber.

9. A tilt bag indicating device as recited in claim 8, wherein said fluid indicating member is a color changeable component when wet.

10. A tilt bag indicating device as recited in claim 8, wherein said fluid indicating member is a sponge.

11. A tilt bag indicating device as recited in claim 8, where said fluid indicating member comprises an antimicrobial agent therewith.

12. A tilt bag indicating device, comprising;
   a urine collection bag having a front wall and a back wall defining a urine collection chamber;
   an inlet for draining urine into said urine collection chamber;
   a tilt indicating chamber attached to the front wall of said urine collection bag, said tilt indicating chamber being in fluid communication with said urine collection chamber through an orifice in said front wall to visibly trap urine therein, if the urine collection bag is tipped so as to permit urine to flow through said orifice and into said indicating chamber;
   said tilt indicating chamber comprising a transparent member attached at its periphery, to said front wall of the collection bag; and
   a vent disposed through said transparent member to facilitate flow of urine into said tilt indicating chamber if said collection bag is tilted too far on its side thus also indicating the possibility of reflux of urine to said inlet.

* * * * *